United States Patent
Yang et al.

(10) Patent No.: US 10,918,856 B2
(45) Date of Patent: Feb. 16, 2021

(54) GRAPHENE BIO-DEVICE FOR ELECTROTHERAPY

(71) Applicants: INCHEON UNIVERSITY INDUSTRY ACADEMIC COOPERATION FOUNDATION, Incheon (KR); Industry-Academic Cooperation Foundation, Yonsei University, Seoul (KR)

(72) Inventors: Sunggu Yang, Seoul (KR); Jong-Hyun Ahn, Seoul (KR); Jejung Kim, Seoul (KR); Wonho Lee, Seoul (KR); Minpyo Kang, Seoul (KR)

(73) Assignee: gBrain Inc., Incheon (KR)

( * ) Notice: Subject to any disclaimer, the term of this patent is extended or adjusted under 35 U.S.C. 154(b) by 135 days.

(21) Appl. No.: 16/030,863

(22) Filed: Jul. 10, 2018

(65) Prior Publication Data
US 2019/0224474 A1    Jul. 25, 2019

(30) Foreign Application Priority Data
Jan. 22, 2018    (KR) .................... 10-2018-0007881

(51) Int. Cl.
*A61N 1/05*    (2006.01)
*A61B 5/04*    (2006.01)
(Continued)

(52) U.S. Cl.
CPC ........ *A61N 1/0531* (2013.01); *A61B 5/04001* (2013.01); *A61B 5/0478* (2013.01);
(Continued)

(58) Field of Classification Search
CPC ............ A61N 1/0531; A61N 1/360645; A61N 1/36135; A61B 5/04001; A61B 5/0478; A61B 5/0464; A61B 5/0494; A61B 5/4848; A61B 5/685; A61B 5/6868; A61B 5/686; A61B 2562/0209; A61B 2562/1028; A61B 2562/125; A61B 2562/164
See application file for complete search history.

(56) References Cited

U.S. PATENT DOCUMENTS

| | | | | |
|---|---|---|---|---|
| 2014/0222103 A1* | 8/2014 | Lauritzen | ........... | A61N 1/36046 607/54 |
| 2016/0007874 A1* | 1/2016 | Ma | ..................... | A61B 5/04001 600/374 |
| 2017/0172446 A1* | 6/2017 | Kuzum | ............. | G01N 33/5438 |

FOREIGN PATENT DOCUMENTS

KR    10-0981184 B1    9/2010

OTHER PUBLICATIONS

Transparent and flexible low noise graphene electrodes for simultaneous electrophysiology and neuroimaging; Nature Communication; pp. 1-10; Published Oct. 20, 2014 to Litt et al. (Year: 2014).*

(Continued)

*Primary Examiner* — Paula J Stice
(74) *Attorney, Agent, or Firm* — Revolution IP, PLLC

(57) ABSTRACT

A graphene bio-device for electrotherapy, includes: a flexible substrate; An electrode made of graphene on the flexible substrate; and an insulation layer on the graphene electrode; wherein the graphene bio-device comprises electrodes for ground, reference, recording and stimulation, wherein the graphene bio-device is measured corticography with low noise and alleviated seizure signals successfully by imposing electrical stimulation.

6 Claims, 6 Drawing Sheets

(51) Int. Cl.
  *A61B 5/00* (2006.01)
  *A61N 1/36* (2006.01)
  *A61B 5/0478* (2006.01)

(52) U.S. Cl.
  CPC .......... *A61B 5/4064* (2013.01); *A61B 5/4094* (2013.01); *A61B 5/4848* (2013.01); *A61B 5/685* (2013.01); *A61B 5/6868* (2013.01); *A61N 1/36064* (2013.01); *A61N 1/36135* (2013.01); *A61B 5/686* (2013.01); *A61B 2562/028* (2013.01); *A61B 2562/0209* (2013.01); *A61B 2562/125* (2013.01); *A61B 2562/164* (2013.01)

(56) References Cited

OTHER PUBLICATIONS

Flexible Neural Electrode Array Based on Porous Graphene for Cortical Microstimulation and Sensing; Scientific Reports; pp. 1-9; published Sep. 19, 2016 to Kuzum et al. (Year: 2016).*
A Low-Power Integrated Circuit for a Wireless 100-Electrode Neural Recording System; IEEE Journal of Solid-State Circuits, vol. 42 , No. 1, Jan. 2007 to Solzbacher et al. (Year: 2007).*

\* cited by examiner

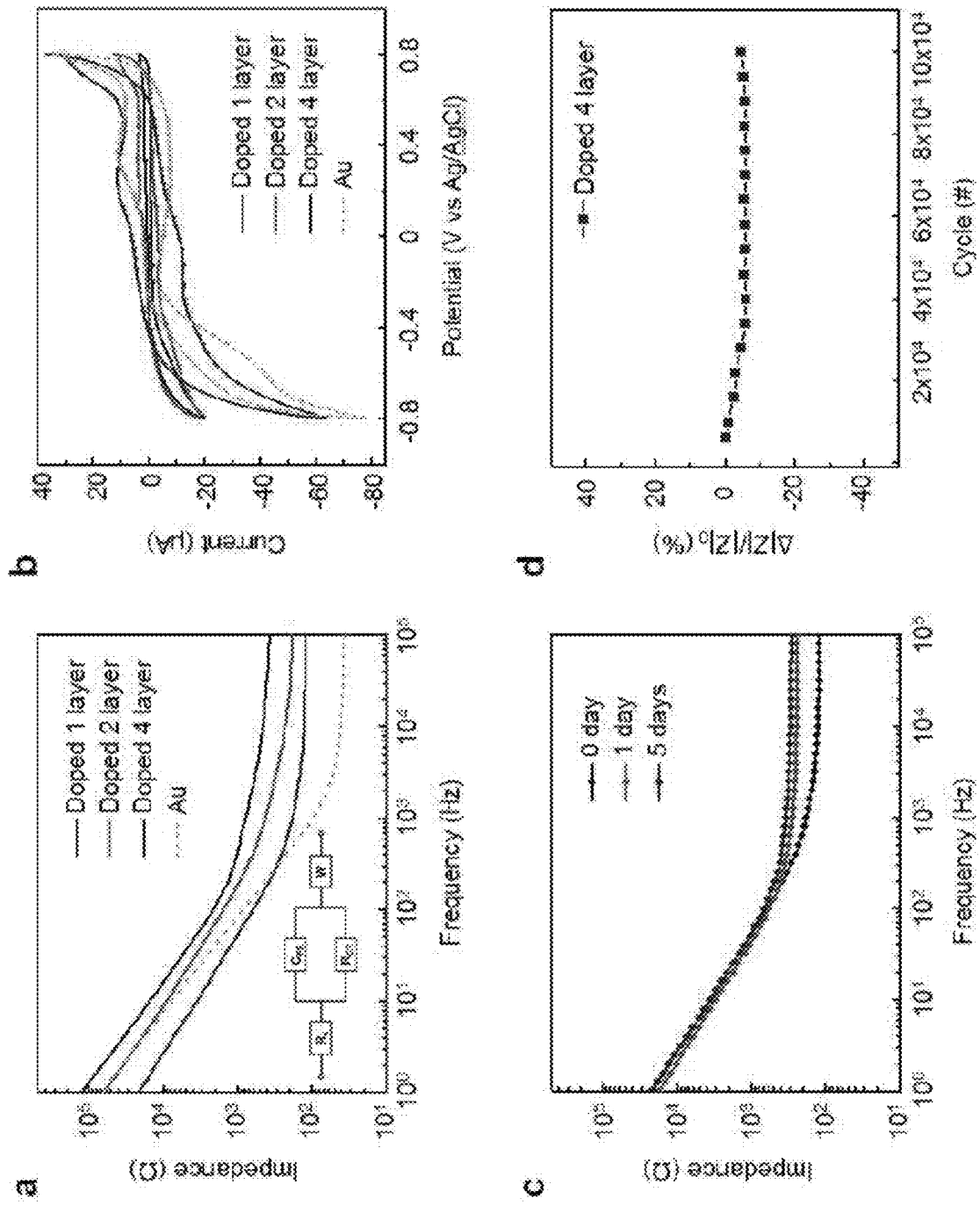
[FIG. 2]

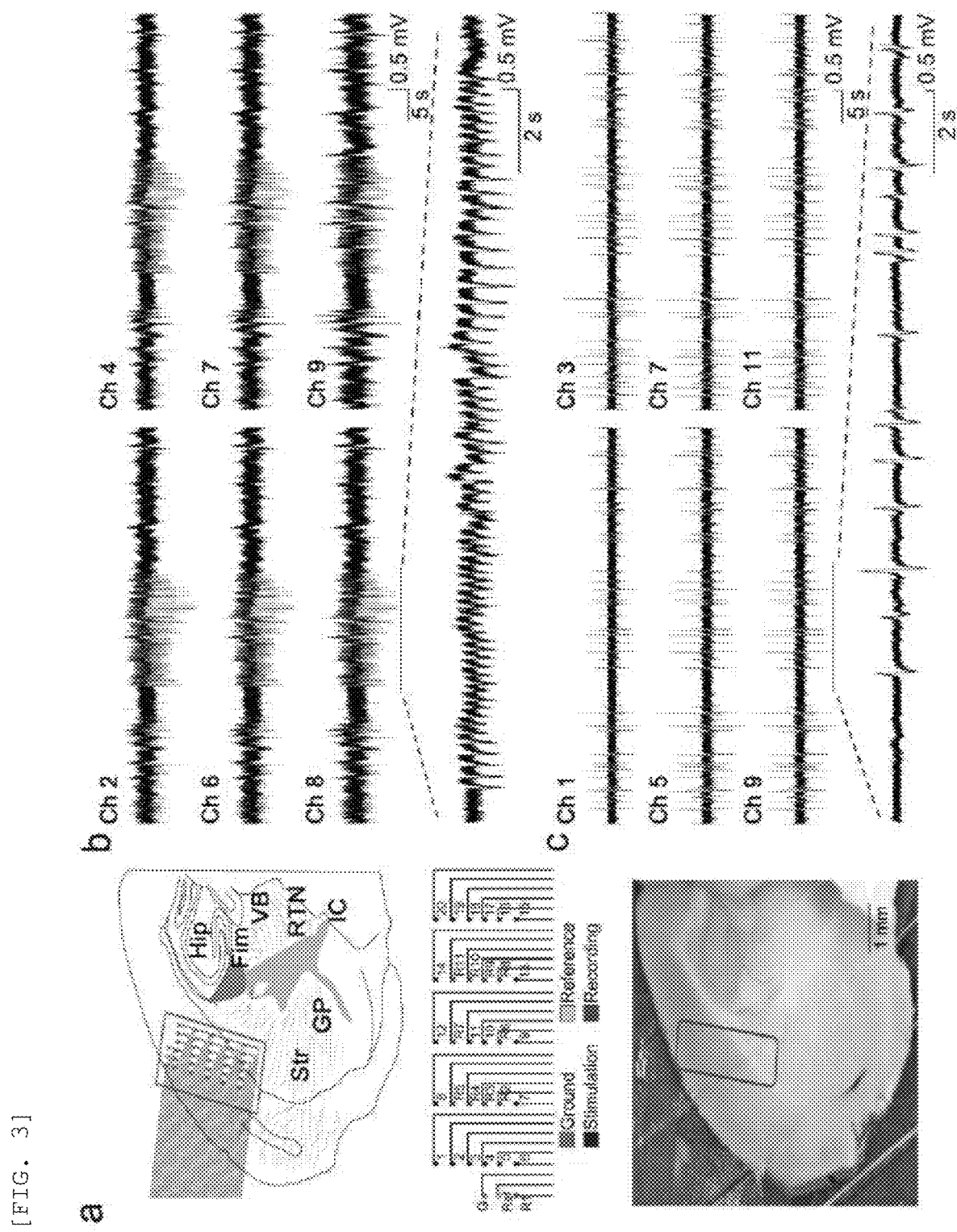
[FIG. 3]

[FIG. 4]
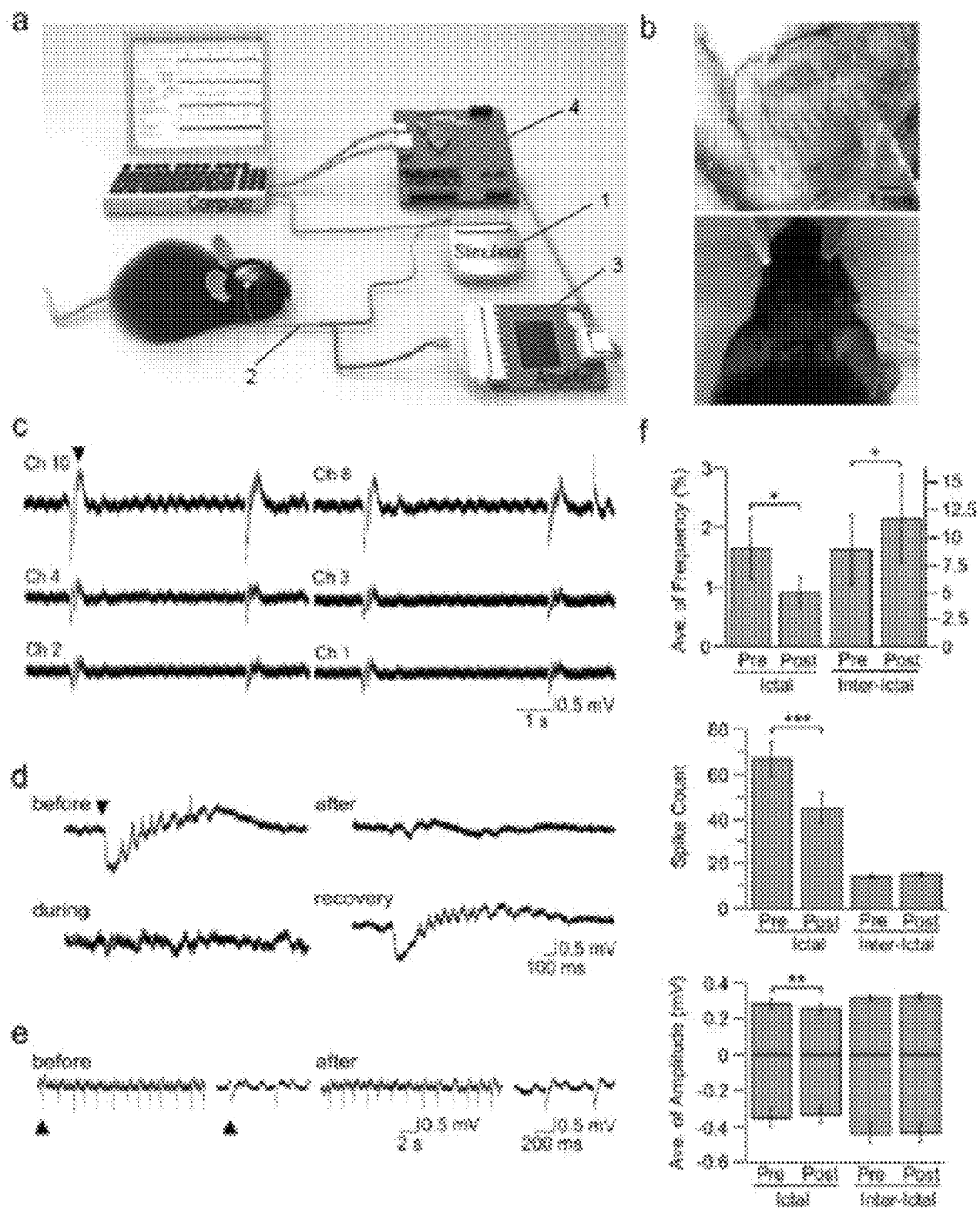

[FIG. 5]
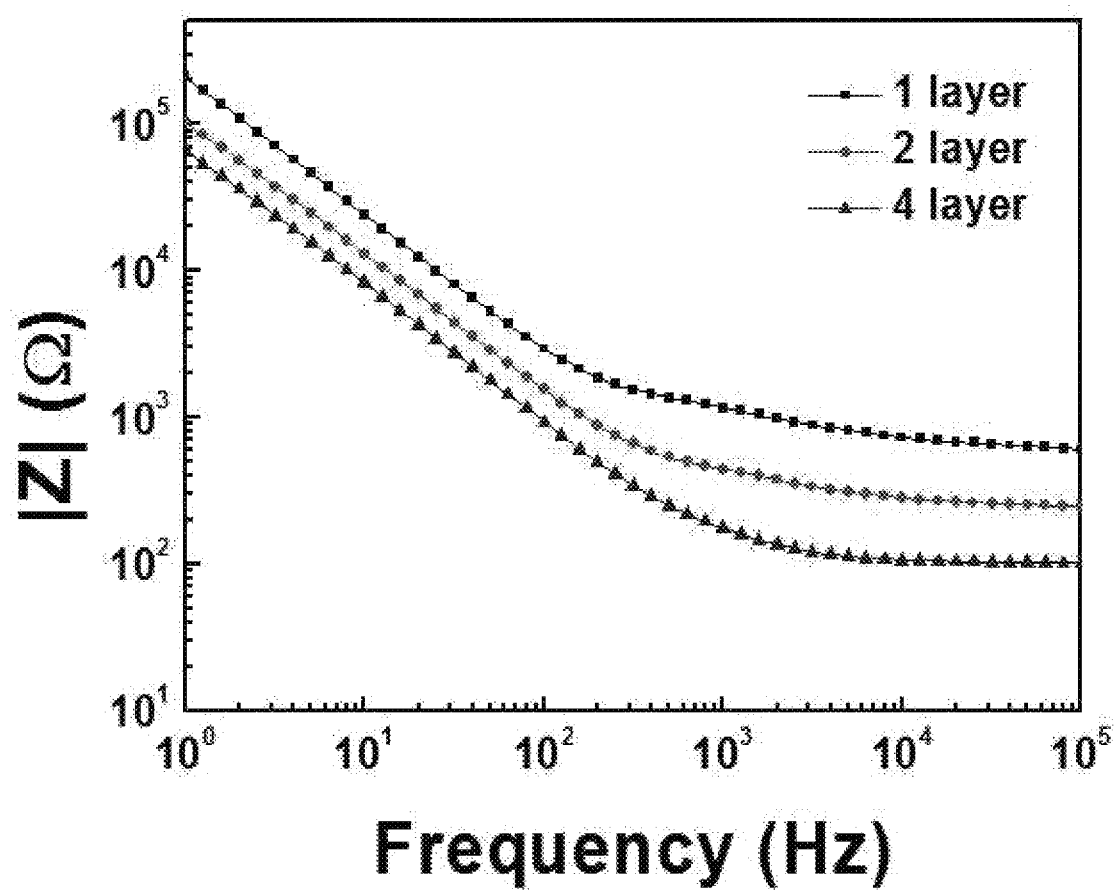

[FIG. 6]
a
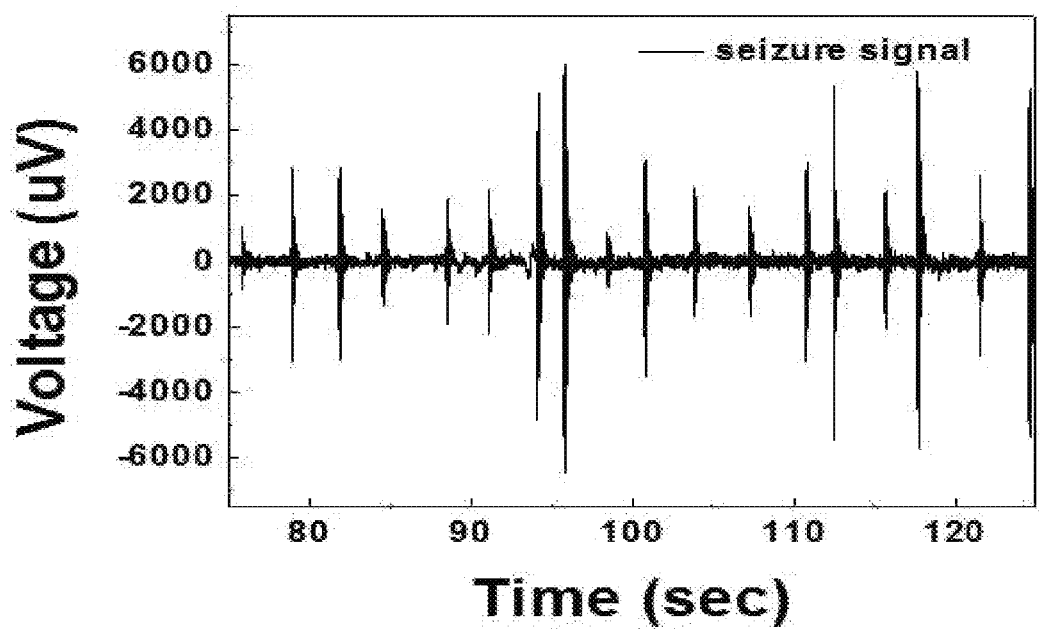
b
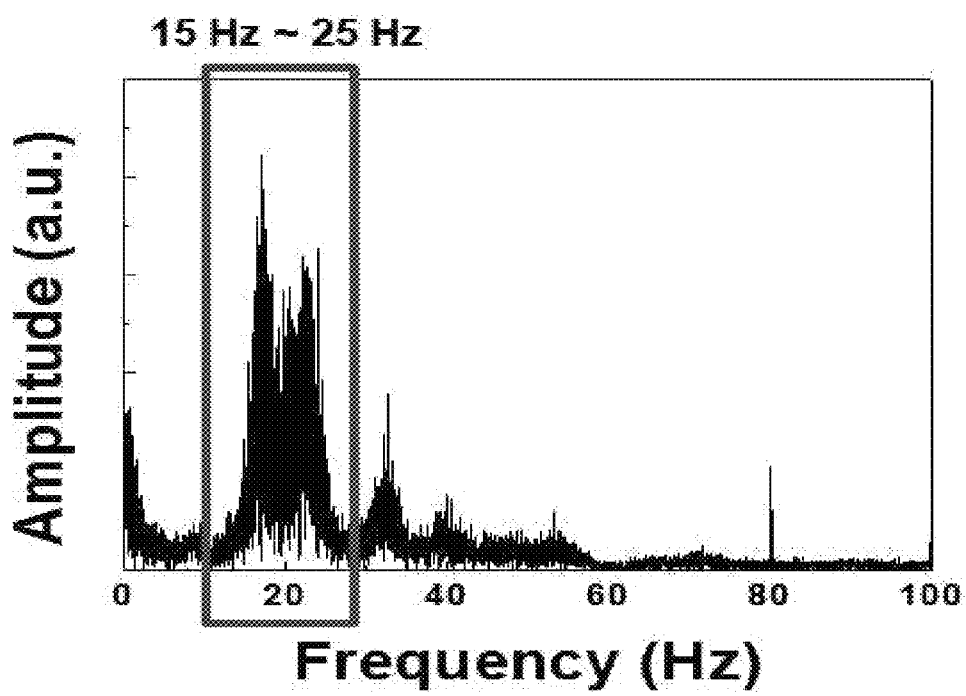

GRAPHENE BIO-DEVICE FOR ELECTROTHERAPY

FIELD OF THE INVENTION

The present invention discloses graphene bio-device for electrotherapy for recording and transmitting electrical signals of a microfabricated graphene microelectrode into cortical areas.

BACKGROUND OF THE INVENTION

Epileptic seizure is a type of neurological disease that is often characterized by repetitive convulsions, and its prevalence is approximately 0.7% worldwide. It involves hyperexcitable activities in neurons, causing malfunctioning in cognition. Subsequently, an episode can trigger secondary physical injuries due to sudden surges of convulsions, which may be life-threatening. It is suggested that the thalamocortical system provides an anatomical network for the rhythmic brain activity of generalized seizure discharges. In vitro and in vivo recording techniques with an animal model of seizures have demonstrated an interaction between the thalamus and neocortex in the occurrence and synchronization of seizure activity. The studies revealed that a reciprocal connection between the thalamic reticular nucleus (TRN) and relay neurons in the thalamus initiated generalized seizures. This intrathalamic oscillation largely propagates and synchronizes with the cortex through the close reciprocality of the thalamocortical network.

The primary treatment for epilepsy is anticonvulsant medications. Chemicals boosting GABAergic inhibitory transmission (e.g., barbiturates and benzodiazepines) have been utilized for epilepsy alleviation. Meanwhile, treatments that reduce hyperexcitable firing (e.g., phenytoin and carbamazepine) are alternatives. In fact, seizures are partially controllable with some medications. However, medications have many side effects due to their global effect across the whole brain. Resection of brain areas in which seizures start is another viable option in some patients. As predicted, the ablation of neural tissues is irreversible and accordingly often associated with severe complications. For those whose seizures do not respond to medication and resection, neurostimulation, such as vagus nerve stimulation (VNS), deep brain stimulation (DBS), and responsive stimulation (RNS), have been considered and beneficially implemented in some patients. Electrical stimulation has the advantages of reversibility and adjustability even in patients who would be thought of as candidates for surgery. VNS, an electrical pulse generator installed along the vagus nerve in the neck, has been effective as an antiepileptic drug therapy in clinical trials. DBS installed into deep brain structures, such as the cerebellum, locus coeruleus, thalamic centromedian nucleus, caudate nucleus, subthalamus, hippocampus, and neocortical seizure foci, has shown some therapeutic effects. RNS, a cranially implanted neurostimulator, detects epileptiform activity via subdural cortical strip leads and treats it via an electrical stimulator before a seizure developsll. These devices have provided supplementary treatment options for patients with intractable seizures yet have unidentified side effects and complications, such as haemorrhage and infection.

Graphene has recently emerged as one of the most investigated two-dimensional materials due to its superior electrical, mechanical, and thermal properties. Therefore, graphene-based electrical devices also have electronic noise, leading to sensor technologies with unprecedented detection sensitivities of neural signals 16-18 and molecules. Moreover, long-term biocompatibility and mechanical flexibility for vulnerable brain tissues are well-known properties of graphene. These promising properties of graphene have increased its use in biomedical applications.

The inventor proposed the use of a graphene electrode for treating epilepsy. A microfabricated graphene microelectrode was placed to record and pass electrical signals into cortical areas. Epileptiform discharges detected with the graphene electrode were eliminated by applying electrical stimulations embedded in a subset of the graphene multichannel array. This graphene technology may allow clinical applications for therapeutic intervention in many brain diseases.

PRIOR ARTS

Patents (Patent 001) Patent No. 10-0981184(KR)

DETAILED DESCRIPTION OF THE INVENTION

Problems to be Solved

The inventor proposed the use of a graphene electrode for treating epilepsy. A microfabricated graphene microelectrode was placed to record and pass electrical signals into cortical areas. Epileptiform discharges detected with the graphene electrode were eliminated by applying electrical stimulations embedded in a subset of the graphene multichannel array. This graphene technology may allow clinical applications for therapeutic intervention in many brain diseases.

Solution

In order to solve the problem, the present invention provides a graphene bio-device for electrotherapy, comprising a flexible substrate; an electrode made of graphene on the flexible substrate; and an insulation layer on the graphene electrode. Further, the graphene bio-device comprises electrodes for ground, reference, recording and stimulation.

The present invention provides a neurostimulating apparatus, comprising the graphene bio-device; a neurostimulator generating sinusoidal high frequency stimulation signals; an amplifier intensifying brain signals from the graphene bio-device; and an interface transmitting the amplified brain signals to a user terminal.

The present invention provides a method for detecting signals from a mammalian brain or a tissue and electrical stimulation to the brain and the tissue.

Benefits of the Invention

Graphene bio-device in the present invention measured corticography with low noise and alleviated seizure signals successfully by imposing electrical stimulation.

BRIEF DESCRIPTION OF THE DRAWINGS

FIG. 2 depicts characteristics of graphene electrodes (a) EIS of doped 1-, 2-, and 4-layer graphene electrodes and a Au electrode for a 1×1 cm² area in aCSF. The inset shows the equivalent circuit model fitted with EIS results. $R_s$ is the resistance of solution; $C_{PE}$ is the constant phase element, which represents electrical double-layer capacitance; $R_{CT}$ is the charge transfer resistance; W is the Warburg diffusion element related with the diffusion of charge in the interface (b) CV curves of the electrodes in aCSF (scan rate: 0.2 Vs-1) (c) Time stability of the doped 4-layer graphene for EIS in aCSF (d) Relative impedance of the doped 4-layer graphene with the cyclic electrical stimulation test.

FIG. 3 depicts in vitro multichannel recording of neuronal activities using graphene electronics (a) A thalamocortical slice on the graphene-based multichannel electrode was illustrated with the electrode's position (top) and topographical design of graphene spots (centre) and was photographed in the recording chamber (bottom). The red box shows a schematic of 30 recording/stimulation spots (centre). Fim, fimbria; GP, globus pallidus; Hip, hippocampus; IC, internal capsule; RTN, reticular nucleus; Str, neostriatum; VB, ventral basal nucleus (b) Ictal-like bursting activities recorded from a graphene-based multichannel electrode. Representative activity in channel #8 is shown as an ictal-like burst that has spikes repeating at 3-5 Hz and lasting 20 s (c) Interictal-like activities recorded from a graphene-based multichannel electrode. Representative activity in channel #9 is shown as an interictal-like spiking that occurs at 1-3 Hz during the 5-min recording.

FIG. 4 depicts in vivo multichannel recording and stimulation of neuronal activities using graphene electronics. (a) a schematic diagram of a recording and stimulation system (b) The photograph of a graphene-based multichannel electrode placed on the somatosensory and/or motor cortical area (c) Ictal-like activities recorded by a graphene-based multichannel electrode. The epileptiform discharges induced by focal application of 15 mM bicuculline were repeated at 5-7 Hz and lasted approximately one second, occurring every 7-15 sec. The epileptiform was reduced by sinusoidal high-frequency stimulation (1V, 100 Hz, 30 sec) through the graphene-based electrode (d) A representative trace of epileptiform activities before, during, after, and recovery of electrical stimulations (e) The interictal-like activity showed no noticeable change even after the sinusoidal high frequency stimulation (f) Histograms of frequency, spike count, and amplitude illustrate that stimulation through the graphene electrode is specific to the epileptiform activity but not to normal synaptic transmission. Error bars indicate the standard error (*P<0.05, P<0.01, and *P<0.001.).

FIG. 5 depicts a graph of EIS of doped 1-, 2-, and 4-layer graphene electrodes.

FIG. 6 depicts a graph of frequency distribution of seizure signals (a) The seizure signals measured by doped 4-layer graphene (b) a graph of Fourier transform of (a) for analyzing signals in frequency.

DETAILED DESCRIPTION OF THE INVENTION

Figure 1:
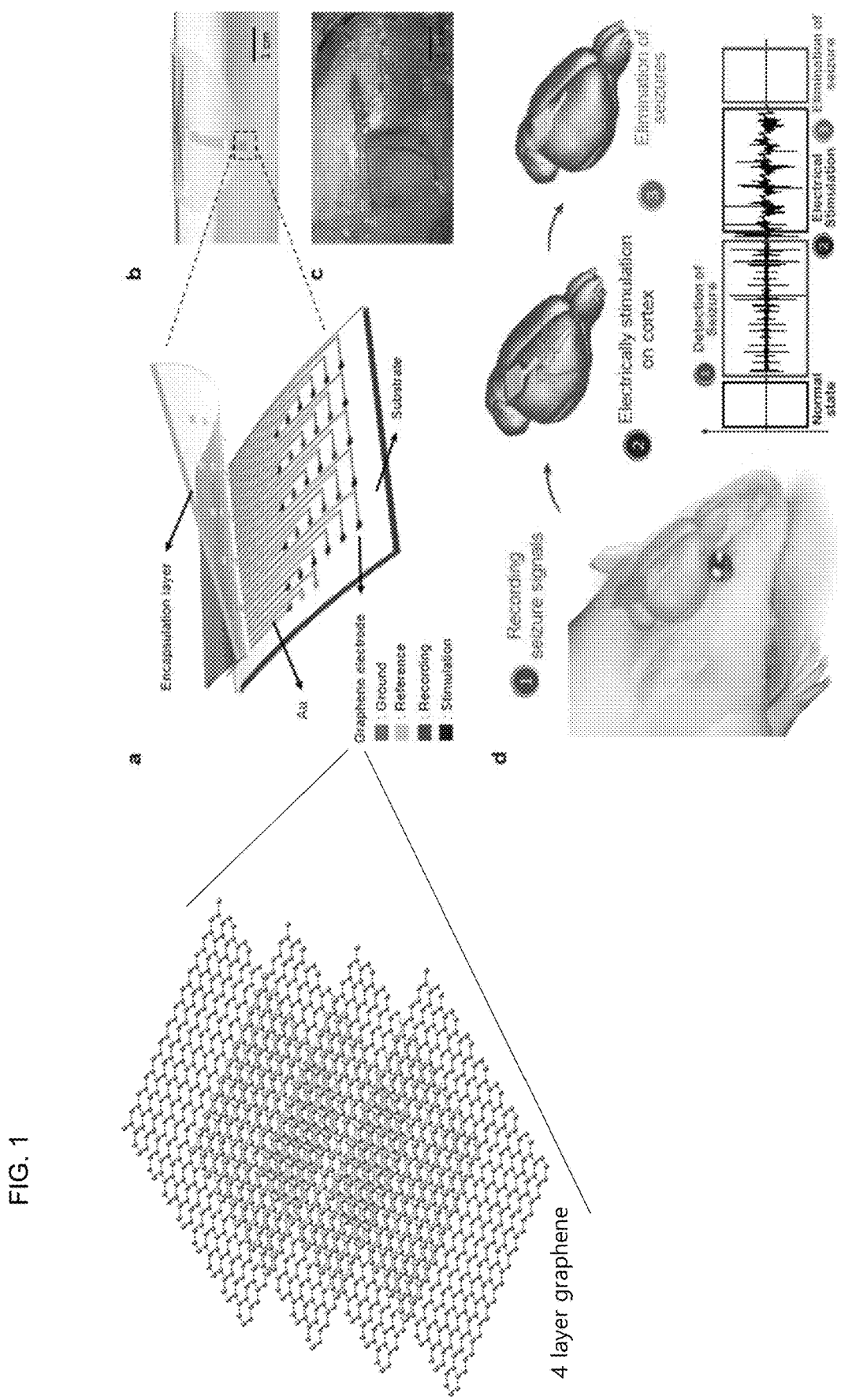
FIG. 1 depicts flexible graphene electrode array and treatment of epilepsy, (a) an schematic diagram of a graphene-based seizure sensor (b) an optical image of a flexible epilepsy treatment sensor on a tube (c) Photograph of a 30-electrode transparent array on the mouse brain (d) a mechanistic illustration of epilepsy treatment using graphene stimulating sensors.

Hereinafter, the present invention will be described in details based on examples.

FIG. 1(a) depicts graphene bio-device for electrotherapy according to an example of the present invention.

The flexible substrate is used as a support substrate for graphene electrodes. The flexible substrate is a film of PET (Polyethylene terephthalate), PC (polycarbonate), PES (polyethersulfone), PI (polyamide), PMMA (polymethyl methacrylate) and COP (cyclo-olefin polymers), and can be made of materials having a flexibility. The flexible substrate has a flexibility depending on material properties.

The graphene is a transparent material for an electrode, and has properties of high charge-transfer (~200,000 cm2/V·s) and high thermal conductivity (~5000 W/mK) and excellent chemical resistance. Additionally, the graphene has no band-gap and thus absorbs all ranges of light wavelength evenly but the width of the graphene is 1-layer. As a result, transparency of the graphene amounts to 97.7% and the graphene has properties of excellent electrical conduction, exceptional mechanical strength (Young's modulus ~1.0 TPa) and high flexibility ($\varepsilon$ ~25%). Based on the properties, the graphene can be used as a material for a transparent electrode.

The graphene can be manufactured in form of a thin film and thus have properties of flexibility and elasticity. Moreover, electrical property of the graphene is not influenced by transformation and thus the graphene can be used as an detect electrode applicable to a flexible apparatus.

The insulation layer can be composed of insulating materials and can be preferably OCR (optical clean resin), OCA (optical clean adhesive) or SU-8.

FIG. 4(a) is a schematic diagram of a stimulation system according to an example of the present invention, which depicts neurostimulation to brain cortex. A bio implant-type medical apparatus such as SCS and DBS comprises a neurostimulator 1 and at least an electrode. The neurostimulator generates pulse signals for stimulating neurons electrically, and the electrode is implanted into a target region and gives neurostimulating signals to the target. The electrode for neurostimulation can be implanted or inserted into a certain region of spinal cord, peripheral nerve or brain although DBS is depicted in FIG. 4(a) as an example. In case of SCS, bio implantable apparatus can be inserted through pectoralis major, abdomen and hip of a patient. Additionally, one or more electrodes in the bio implantable apparatus based on nuerostimulation are typically connected to a long lead 2 depicted in FIG. 4, and the lead play a role of connection between an electrode and a neurostimulator. The electrode in the apparatus is often inserted into subcutaneous tissue but the nerve point to which the electrode reaches out is located into a deeper site of a body more frequently. Consequently, a connector between a neurostimulator and a lead exists, and the connector and the neurostimulator places outside of a body frequently.

The neurostimulator can further comprise an amplifier 3. The amplifier can intensify electrical signals of a brain detected for a recording electrode in the graphene biodevice. Moreover, the neurostimulator in the present invention can further comprise an interface 4 transmitting the brain signals intensified by the amplifier to a user terminal.

The terminal can provide the detected brain signals visually, and further comprise a display and a speaker. For example, the terminal can be a cell phone, a smart phone, laptop computer, desktop computer, PDA (personal digital assistants), PMP (portable multimedia player), a navigator and a digital TV.

Hereinafter, the present invention is described in details based on examples.

EXPERIMENTS

1. Graphene Electrode Fabrication and Characterization

Monolayer graphene was grown on 25 μm thick Cu foil using the CVD method. The roll of copper foil (thickness: 25 μm, size: 210×297 mm$^2$, Alfa_Aesar Co.) is loaded into a tubular quartz tube and then heated to 1,000° C. under atmospheric pressure. After the graphene had grown up on the Cu foil by supplying a gas mixture including carbon source ($CH_4$:$H_2$:He=50:15:1000 sccm), it was rapidly cooled to room temperature at a rate of ~10° C./s with flowing $H_2$ or He while moving furnace and then a graphene film grown up on the Cu foil was produced.

To make multilayer graphene electrodes, PMMA was used for supporting layers on graphene. After synthesizing graphene on Cu foil and spin-coating the PMMA, the film was floated on about 0.1M $(NH_4)_2S_2O_8$ solution. Then the Cu was removed and the PMMA/G film was lifted up using another Cu foil with grown graphene. A multilayer film was formed repeating the etching and the transfer process. The PMMA-coated graphene obtained after the etching of Cu foil in aqueous ammonium persulfate solution was transferred onto another graphene on Cu foil. Then, the graphene was transferred onto a SU-8 epoxy substrate. The transferred graphene was patterned using photolithography and oxygen plasma etching. Nitric acid was used for chemical doping of graphene.

2. Thalamocortical Slice Preparation

All animal handling procedures were approved by the Institutional Animal Care and Use Committee at Incheon National University. C57BL/6 mice (postnatal age: 3-6 weeks) for brain slices were deeply anaesthetized with 2% isoflurane. The brain was quickly removed and placed into chilled (4° C.), oxygenated (5% $CO_2$ and 95% $O_2$) slicing medium containing (in mM): 212 sucrose, 5 KCl, 1.23 $NaH_2PO_4$, 26 $NaHCO_3$, 11 glucose, 1.5 $MgCl_2$, and 2.5 $CaCl_2$. The thalamocortical slices (400 μm) containing somatosensory cortex and thalamus were cut according to the protocol (Agmon, A. et al. Neuroscience 41, 365-379 (1991)). Brain slices were then transferred to a holding chamber containing oxygenated physiological saline made up of (in mM): 124 NaCl, 4 KCl, 1.23 $NaH_2PO_4$, 26 $NaHCO_3$, glucose, 1.5 $MgCl_2$, and 2 $CaCl_2$. After about 1 hour of recovery, individual slices were transferred to a recording chamber. Oxygenated physiological saline was continuously superfused at a rate of 1.5 ml/min. The focal injection of bicuculline (1 mM) into thalamocortical slices induced two main types of spontaneous activity: ictal-like monotonic bursts of 3-5 Hz, similar to human generalized seizures in terms of frequency and duration of EEG recordings, and interictal-like activities.

3. In Vivo Animal Surgery

An in vivo experiment was conducted with a halothane-anaesthetized mouse (1200 mg/kg, i.p.) with its head fixed in a stereotaxic apparatus. Five-week-old male mice were used in the experiments. A craniotomy exposed a 5×5 mm$^2$ region of the cortex. The cerebral spinal fluid (CSF) was drained to reduce the probability of cerebral oedema. In this procedure, muscles were blunt-dissected over the occipital skull to expose the cisterna magna above the axis at the top of the spinal cord. The dura was slit with a sharp knife, and a cotton wick was used to drain the CSF. With the head stabilized in an eye clamp and stereotaxic apparatus, a scalp incision was made under clean surgical conditions, and a craniotomy was performed by cutting out a window of bone from the calvaria. This enabled neurophysiological recording in the target zone of the brain. The dura mater is routinely resected during animal recording; it was left intact with graphene electrodes introduced transdurally in animal recording studies.

4. In Vitro and In Vivo Neural Recordings

The neural recording setups were built in-house as illustrated in FIG. 4a. The brain signals detected by graphene-based electronics were processed using a multichannel neural amplifier and an acquisition system (Intan Technologies, LCC, Los Angeles, Calif., USA), while the stimulations were provided by stimulators (NI-9263, National Instruments, Austin, Tex., USA). Neural recording data were analyzed offline using Matlab.

Result

The fabrication and feasibility of graphene electrodes for electrotherapy are illustrated in FIG. 1. An electrode array consists of 10 and 20 channels for recording and electrotherapy, respectively. The graphene was grown on thin copper foil using conventional chemical vapour deposition (CVD) and was then transferred to SU-8 epoxy film (~5 μm thickness) using a polymethyl methacrylate (PMMA) supporting layer. The transferred graphene was patterned using photolithography and oxygen plasma etching, and it was chemically doped by exposure to nitric acid vapour for improving its electrical conductivity. All non-conductive areas and gold lines were encapsulated with a thin SU-8 epoxy layer (~0.5 μm) (FIG. 1a). After the fabrication, the array was directly mounted onto the cortex of the mouse brain. A key feature of the graphene used here is that it has a desirable surface topography for the brain cortex for enduring severe deformation of the cortex. This property is due to its low flexural rigidity (FIGS. 1b and 1c). Once this ultra-thin graphene electrode array detects epileptic discharges throughout the surface of the cortex, electrical pulses embedded in a subset of the multichannel array will be transferred into the site of epilepsy to stop bursting discharges.

The inventors in the present invention examined the electrochemical properties of four different types of electrodes: mono-, bi-, and four-layer graphene and gold. As the number of the stacked layers increased, the impedance of the graphene electrodes decreased, just like a gold electrode (FIG. 2a and FIG. 5). The impedance of the doped four-layer graphene electrode showed lower values in the local field potential range (1-100 Hz), in which the majority of the epileptic discharges appeared. Lower impedance in the low frequency range can help the flow of electrical signals, including more efficient neuronal spiking, and thus reduces electronic noise. Next, to investigate whether our fabricated graphene electrode showed better performance in charge transfers, cyclic voltammetry (CV) was employed with the four different electrodes. Consequently, the four-layer graphene electrode had a specific capacitance of 326.7 F/g, which is much higher than that of the gold electrode (77.5 F/g) (FIG. 2b and Table 1&2).

TABLE 1

| | $C_{PE}$ (S × s$^n$) | | | |
|---|---|---|---|---|
| | Q | n | $R_{CT}$ (Kohm) | $Z_W$(W) (S × s$^{1/2}$) |
| Au | 2.52 × 10$^{-6}$ | 0.97 | 1,220 | 5.77 × 10$^{-4}$ |
| Doped 4L graphene | 1.03 × 10$^{-5}$ | 0.85 | 109 | 2.27 × 10$^{-4}$ |

TABLE 2

| | Specific capacitance(F/g) |
|---|---|
| Doped 1L | 288.2 |
| Doped 2L | 219.4 |
| Doped 4L | 326.7 |
| Gold | 77.49 |

The specific capacitance was calculated based on [Formula 1].

$$C = \frac{\int IdV}{\Delta V \times m \times s} \quad \text{[Formula 1]}$$

I is current density (A/cm$^2$), $\Delta V$ is a range of Voltage scan, m is electrode mass and s is scan velocity (mV/s).

This indicated that the four-layer graphene electrode likely enhances the amount of charge transfer when electrical stimulation is applied. Such an improvement of charge transfer ability can allow the dimensions of the electrodes to decrease, which has an impact on the reduced power consumption and thus a low probability of physical damage to the brain by electrical stimulation. To examine the long-term stability of the doped four-layer graphene electrode in artificial cerebrospinal fluid (ACSF), electrochemical impedance spectroscopy (EIS) was measured at Day 0, Day 1, and Day 5 (FIG. 2c). the change of impedance in a particular frequency range, i.e., from 15 to 25 Hz was observed, which was the most distributed frequency range of the power of electrical signals when a seizure was detected (FIG. 6). It was observed that the doped four-layer graphene electrode had negligible degradation (5.5% on Day 1 and Day 5). Moreover, relative impedance had a slight change of about 5% under a cyclic electrical stimulation test over 9×10$^4$ times (FIG. 2d). These results show that our fabricated graphene electrode can operate on the brain with long-term stability.

To test the detectability of epileptiform activity by the four-layer graphene multichannel electrode, the 60×60 pmt graphene electrodes were mounted onto thalamocortical slices (FIG. 3a).

Two types of spontaneous activities, such as ictal-like bursting and interictal-like activities, were observed within 5 min after focal application of 1 mM bicuculline, a GABA$_A$ receptor antagonist. There were 5-20 second long ictal-like bursting activities (FIG. 3b) and interictal-like activities (FIG. 3c) in most recording units. These data suggested that the device is capable of capturing simultaneous fast-spiking responses of cortical ensembles.

Next, in vivo brain responses were obtained with the graphene electrodes in anaesthetized animals. The graphene device was placed on the somatosensory and/or motor cortical area (FIGS. 4a and 4b). The flexibility of the epidermal graphene enabled sampling of neuronal signals on the wrinkled surface of the cortex. Focal application of 15 mM bicuculline induced two types of spontaneous activities that were similar to those from in vitro brain slice experiments in ten animals tested: ictal- and interictal-like responses. In two responses, the seizure-like activities were found on most recording spots of cortical areas (FIG. 4c).

Amplitudes varied presumably depending on the degree of contact of graphene on the cortex, the sites affected by bicuculline, or both. Particularly, the pattern of brain signals in a seizure episode was similar in all spots.

Next, the inventors identified whether the epileptiform activity could be eliminated by sinusoidal high frequency stimulation (sHFS). The stimulating parameters of amplitude (1 V), frequency (100 Hz), and duration (30 sec) were adapted from the previous references using the DBS system. They were designed for developing therapeutic devices for epileptic seizures. The sHFS stimulation blocked bursting activities up to 2 min after the stimulation (FIG. 4d). Then, the suppressed responses were back to the bicuculline-induced condition, suggesting that the high frequency stimulus itself did not cause tissue or response damage. In a subset of experiments, the same stimulation protocol was applied to interictal-like activities to test the effect of sHFS on normal signal transmission. The sHFS stimulation did not block the interictal-like activity (FIG. 4e). Rather, it showed the selectivity of sHSF on epileptiform activities. The effect of sHFS on ictal- and interictal-like activities was analyzed with three parameters: frequency, spike count, and amplitude. The frequency was decreased from 1.68±0.5% to 0.94±0.27% in ictal-like bursting (P<0.05, paired t-test) but not in the interictal-like activities, which changed from 8.80±3.08% to 11.54±3.91% (P<0.05, FIG. 4f, top). The spike count of ictal-like bursting was significantly reduced from 66.64±7.92 to 44.91±6.67 (P<0.001, FIG. 4f, centre), while that of interictal-like activities remained unaffected (P>0.1). The average amplitude of ictal-like bursting was reduced from 0.28±0.03 (upward deflection) and ~0.35±0.05 mV (downward deflection) to 0.26±0.02 and ~0.33±0.05, respectively (P=0.003, FIG. 4f, bottom), while the amplitudes of interictal-like activities was not changed (P>0.1, FIG. 4f, bottom).

Discussion

The present invention integrates ultrathin and flexible graphene into an array of electrocorticography, which realizes comprehensive cortical ensemble activities (for diagnosis purposes) and treat brain diseases (for treatment purposes). The multichannel graphene electrode in the present invention successfully detected brain signals with high-throughput spatiotemporal resolution and stopped a drug-induced ictal-like activity. Such integration of simultaneous recording and stimulation could lead to a fundamental change in approaches for diagnostic and therapeutic biomedical devices.

sHFS was used to control abnormal neuronal activities, such as movement disorders, seizures, and psychiatric symptoms in the past. sHFS mimicked by AC stimulation typically has the intensity of 1-10 V and a pulse of 100-165 Hz in a clinical DBS system, which is comparable to the protocol of the present invention for epidermal electronics (1 V, 100 Hz for an animal model). The inventors implemented a sinusoidal wave as the envelope of carrier frequency because suppressive thresholds on epileptiform activities were lower in sHFS than in pulse train HFS (pHFS). In fact, sinusoidal stimulation efficiently suppressed somatic neural activity and the axonal conduction of bursting neurons. The results were different from studies using pHFS, which has suppressive effects on axonal conduction and synaptic efficacy. For example, the steeper rise time, as in pulse train stimulation, may boost an excitatory response. It is interesting that the sHFS has been associated with increases in extracellular potassium in the epileptic brain. It is well known that elevated extracellular potassium concentrations reduce action potential amplitudes, depress presynaptic potentials, affect axonal signaling and subsequently cause a depolarization blockade. On the other hand, sHFS left normal electrical signals unaffected in our study. sHFS can be a useful parameter for therapeutic stimulation, as it shows a selective effect on epileptic discharges (FIG. 4).

DBS and RNS penetrate into the brain, which frequently causes physical damage and harmful immune responses. The present invention introduce epidermal electronics to control epilepsy noninvasively. The metal Ag is used in conventional electrodes and is often corrosive, being easily degraded through sulfidation and oxidation in various biological environments. Because of its toxicity and instability, bare Ag is limited for use in neural implants. Meanwhile, when Ag is coated with graphene, electrochemical reactions on the Ag surface can be eliminated. CV and potentiodynamic polarization tests have shown that graphene coating significantly reduces Ag corrosion in phosphate-buffered saline. Consistent with the previous study, the present invention showed that the graphene electrodes have long-lasting stability and biocompatibility. Importantly, epidermal graphene on the cortical surface, where there are abundant digital parts of neurons such as axons and dendrites, might be less harmful than electrodes penetrating into the deep areas of the brain where damageable cell bodies are localized. Lastly, the mechanical flexibility and compliance of the epidermal electronics guaranteed reliable detectability of neural signals.

Current epidermal electronics should be further developed according to structure and function to better fit human cortex. Once graphene-based, foldable electronics detect epileptic discharges on the surface of the cortex, electrical pulses embedded in a subset of the multichannel array can be given to stop epileptic discharges. A portable, wireless brain stimulator that fits in a pocket will switch the power for the electrical pulses for convenient use. The present invention is a useful tool for epilepsy and may also be a therapeutic instrument for patients suffering from several neuronal disorders, such as Parkinson's disease, schizophrenia, tinnitus and depression.

What is claimed is:
1. A neurostimulating apparatus, consisting of:
   a graphene bio-device consisting of:
      a flexible substrate which is PMMA (polymethylmethacrylate);
      doped four-layer graphene electrodes on the flexible substrate forming an electrode array having 30 channels for recording and electrotherapy; and
      an insulation layer on the doped four-layer graphene electrodes which comprise ground electrodes, reference electrodes, recording electrodes and stimulation electrodes;
   a neurostimulator generating sinusoidal high frequency stimulation signals and enabling the graphen bio-device to provide neurostimulating signals to a target, wherein the sinusoidal high frequency stimulation signals include an amplitude of 1V, a frequency of 100 Hz, and a duration of 30 sec;
   an amplifier intensifying brain signals from the graphene bio-device; and
   an interface transmitting the amplified brain signals to a user terminal,
   wherein the graphene bio-device, the neurostimulator, the amplifier, and the interface are connected to each other by a lead.
2. A method for detecting signals from a mammalian brain or a mammalian tissue and electrical stimulation to the brain or the tissue using the graphene bio-device claim 1.
3. The method of claim 2, wherein the electrical stimulation is sinusoidal high frequency stimulation (sHFS).
4. The neurostimulating apparatus of claim 1, wherein the insulation layer is OCR (optical clean resin), OCA (optical clean adhesive) or SU-8.
5. The neurostimulating apparatus of claim 1, wherein the doped four-layer graphene electrodes layers have a specific capacitance of 326.7 F/g.
6. The neurostimulating apparatus of claim 1, wherein the graphene bio-device is placed in somatosensory area or motor cortical area.

* * * * *